United States Patent [19]

Ono et al.

[11] 4,233,307
[45] Nov. 11, 1980

[54] SPIRO-4'-PIPERIDINE COMPOUNDS AND THEIR PHARMACEUTICAL COMPOSITIONS

[75] Inventors: Keiichi Ono, Osaka; Kikuo Sasajima, Saitama; Junki Katsube, Toyonaka; Hisao Yamamoto, Kobe, all of Japan

[73] Assignee: Sumitomo Chemical Company, Limited, Osaka, Japan

[21] Appl. No.: 910,537

[22] Filed: May 30, 1978

[30] Foreign Application Priority Data

Feb. 13, 1978 [JP] Japan ................................. 53/15778

[51] Int. Cl.³ ................... A61K 31/445; C07D 471/10
[52] U.S. Cl. ...................................... 424/267; 546/16; 546/17; 546/208
[58] Field of Search ........................... 546/17; 424/267

[56] References Cited
U.S. PATENT DOCUMENTS 3,299,075  1/1967  Weisbach .............................. 260/293

OTHER PUBLICATIONS

Burger, A. (ed.) "Medincinal Chemistry", 2nd ed., Interscience Publishers, Inc., N. Y. 1960.

Primary Examiner—Donald G. Daus
Assistant Examiner—Lisa Jones
Attorney, Agent, or Firm—Stevens, Davis, Miller & Mosher

[57] ABSTRACT

Spiro amine derivatives having excellent antihypertensive activity and central nervous system depressant activity, and represented by the formula:

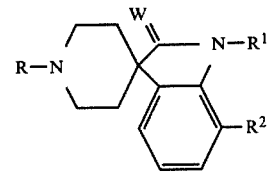

and their preparation and use.

12 Claims, No Drawings

SPIRO-4'-PIPERIDINE COMPOUNDS AND THEIR PHARMACEUTICAL COMPOSITIONS

The present invention relates to spiro amine derivatives having antihypertensive activity and central nervous system depressant activity, and to preparation and use thereof.

More particularly, the present invention provides novel spiro amine derivatives of the general formula:

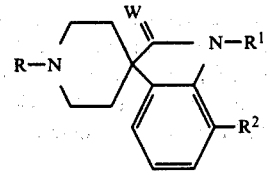
(I)

wherein $R^1$ is a hydrogen atom, a $C_1$-$C_4$ alkyl group, a phenyl group or a phenyl group substituted with a halogen atom, a $C_1$-$C_4$ alkyl group or a $C_1$-$C_4$ alkoxy group, $R^2$ is a hydrogen atom, or $R^1$ and $R^2$, when taken together, may form a $C_1$-$C_4$ alkylene group, W is an oxygen atom or two hydrogen atoms and R is a group of either one of the formulae:

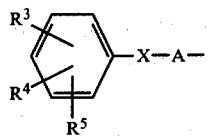

(wherein A is a $C_1$-$C_4$ alkylene, X is a carbonyl group, an oxygen atom, a single bond linkage, the formula >CH—OH or the formula —CH=CH— and $R^3$, $R^4$ and $R^5$ are each independently a hydrogen atom, a $C_1$-$C_4$ alkyl group, a $C_1$-$C_4$ alkoxy group, a benzyloxy group, a halogen atom or a hydroxy group) and $$R^6—\underset{\underset{OH}{|}}{C}HCH_2—$$

[wherein $R^6$ is a group of either one of the formulae:

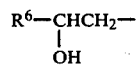

(wherein $R^7$ is a hydrogen atom, a halogen atom, a nitril group, a $C_1$-$C_4$ alkyl group, a $C_1$-$C_4$ alkoxy group or a hydroxyl group),

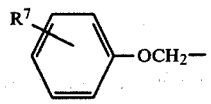

(wherein $R^7$ is as defined above) and

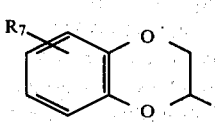

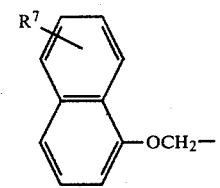

(wherein $R^7$ is as defined above)], and the non-toxic pharmaceutically acceptable acid addition salts thereof.

In the definitions as used herein by the term "halogen" is meant a chlorine, fluorine, bromine or iodine atom: by the term "$C_1$-$C_4$ alkyl" is meant straight or branched chain alkyl groups having from one to four carbon atoms (e.g. methyl, ethyl, isopropyl, butyl, etc.): by the term "$C_1$-$C_4$ alkoxy" is meant alkoxy groups having from one to four carbon atoms (e.g. methoxy, ethoxy, isopropoxy, etc.): by the term "$C_1$-$C_4$ alkylene" is meant methylene, ethylene, trimethylene and tetramethylene.

It has been found that the novel spiro amine derivatives of the formula (I) as defined above have a hypotensive activity and are useful as anti-hypertensive agents. They also have a central nervous system depressant activity and are useful as tranquilizers and antipsychotic agents.

Among the spiro amine derivatives of the formula (I) the preferred compounds are, with respect to the formula (I), those in which W is an oxygen atom. Further more preferred compounds may be represented by the formulae:

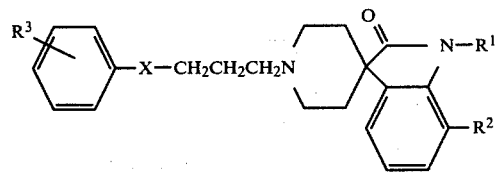

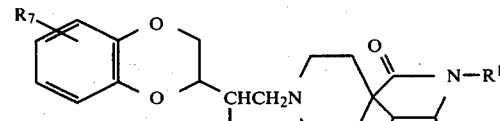

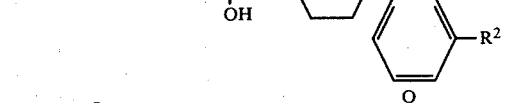

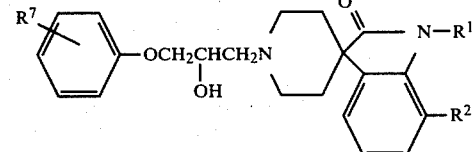

wherein $R^1$, $R^2$, $R^3$ and $R^7$ are each as defined above, and X is a carbonyl group or the formula >CH-OH.

For example, 1'-[3-(4-fluorobenzoyl)propyl]-1-methyl-2-oxo-indoline-3-spiro-4'-piperidine has a potent hypotensive action at low dosages (0.1 mg/kg-0.3 mg/kg ip).

Accordingly, a basic object of the present invention is to provide novel spiro amine derivatives (I) having central nervous system depressing activity and antihypertensive activity. Another object of the invention is to provide process for producing the spiro amine derivatives (I). These and other objects will be apparent to those skilled in the art to which the present invention pertains from the foregoing and subsequent descriptions.

According to the present invention, the spiro amine derivatives (I) can be prepared by reacting a compound of the formula:

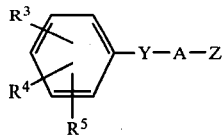

wherein Y is a carbonyl group, a protected carbonyl group, an oxygen atom, a single bond linkage, the formula >CH—OH or the formula —CH=CH—, Z is a halogen atom and A, $R^3$, $R^4$ and $R^5$ are as defined above, or a compound of the formula:

$$R^6—B \quad (III)$$

wherein $R^6$ is as defined above and B is a group of either one of the formulae:

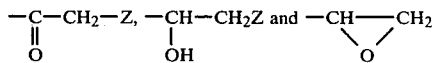

(wherein Z is as defined above) with a spiro amine derivative of the formula:

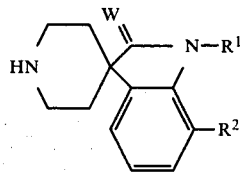

wherein $R^1$, $R^2$ and W are each as defined above, optionally followed by reduction of a carbonyl group, or by hydrolysis of a protected carbonyl group.

The spiro amine derivatives in which $R^3$, $R^4$ or $R^5$ is a hydroxy group with respect to the formula (I), can also be prepared by debenzylation of the corresponding benzyloxy derivatives.

The condensation reaction is usually carried out in an inert solvent such as an aromatic hydrocarbon (e.g. benzene, toluene, xylene), an amide (e.g. dimethylformamide, dimethylacetamide), an ether (e.g. dioxane, tetrahydrofuran), an alcohol (e.g. ethanol, n-butanol, propanol, amylalcohol), an alkanone (e.g. acetone, butanone, methylisobutylketone) or dimethylsulfoxide at a temperature within a range of 0° C. to the boiling point of the solvent. Preferably, there may be used a basic substance such as an alkali hydrogen carbonate (e.g. sodium hydrogen carbonate, potassium hydrogen carbonate), an alkali carbonate (e.g. sodium carbonate, potassium carbonate), an alkali hydroxide (e.g. sodium hydroxide, potassium hydroxide) or an organic amine (e.g. pyridine, triethylamine) as an acid binding agent. There may be also used a small amount of a reaction accelerating agent such as potassium iodide.

The hydrolysis can be carried out by conventional acid hydrolyzing procedure. For instance, it can be accomplished by treating the protected compound with an acidic substance such as a mineral acid (e.g. hydrochloric acid, sulfuric acid, phosphoric acid), an organic acid (e.g. oxalic acid, tartaric acid) or an acidic ion exchange resin in water or an alkanol (e.g. methanol, ethanol, propanol), usually under a mild condition, e.g. at room temperature. Further, it may be accelerated by elevation of the temperature.

The reduction of a carbonyl group can be carried out in an inert solvent such as an ether (e.g. diethylether, tetrahydrofuran, dioxane), an alcohol (e.g. methanol, ethanol, isopropanol), benzene, toluene or water at a temperature within a range of room temperature to the boiling point of the solvent.

Suitable reducing agents which are preferably employed in the reaction are metal hydride complexes such as lithium aluminum hydride, sodium borohydride, bis-(2-methoxyethoxy) aluminum chloride or sodium aluminum diethyl dihydride, palladium on charcoal or platinum oxide.

The spiro amine derivatives of the formula (IV) can be prepared by condensation of an oxindole derivatives of the formula:

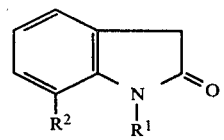

wherein $R^1$ and $R^2$ are each as defined above, with a dihalide of the formula:

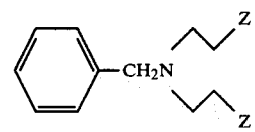

wherein Z is as defined above, optionally followed by reduction of an amide group to give a compound of the formula:

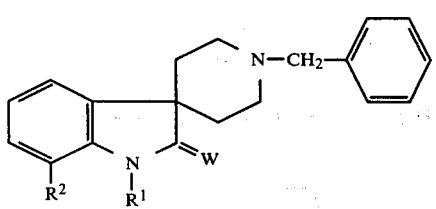

wherein $R^1$, $R^2$ and W are each as defined above, followed, by debenzylation of the latter.

The condensation reaction of the compound (V) with the compound (VI) is carried out in an inert solvent such as an aromatic hydrocarbon (e.g. benzene, toluene, xylene) at temperature within a range of room temperature to the boiling point of the solvent. Suitable condensation agents are metal hydride (e.g. sodium hydride, calcium hydride), metal alcoxide (e.g. sodium ethoxide, potassium t-butoxide) or sodium amide.

The debenzylation can be carried out by a conventional catalytic hydrogenation procedure, or by treating the compound (VII) with a compound of the formula:

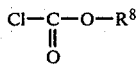
(VIII)

wherein $R^8$ is a $C_1$-$C_4$ alkyl group or a benzyl group, followed by hydrolysis or hydrogenolysis of the compound of the formula:

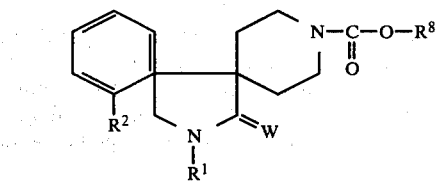
(IX)

wherein $R^1$, $R^2$, W and $R^8$ are each as defined above.

Specific examples of the spiro amine derivatives (I) are as follows:

1′-(2-hydroxy-3-phenoxypropyl)-1-methyl-2-oxoindoline-3-spiro-4′-piperidine

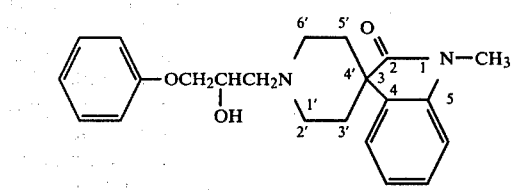

1′-(2-hydroxy-3-phenoxypropyl)-1-ethyl-2-oxoindoline-3-spiro-4′-piperidine

1′-(2-hydroxy-3-phenoxypropyl)-1-methyl-indoline-3-spiro-4′-piperidine

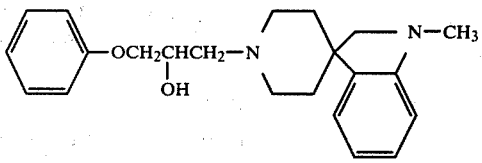

1′-(2-hydroxy-3-phenoxypropyl)-2-oxo-1,2,5,6-tetrahydro-4H-pyrrolo[3,2,1-ij]quinoline-1-spiro-4′-piperidine

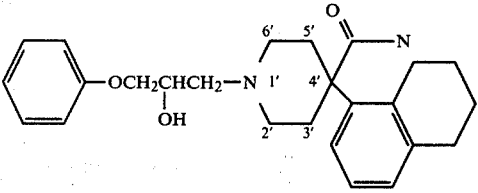

1′-[2-(1,4-benzodioxane-2-yl)-2-hydroxyethyl]-1-methyl-2-oxo-indoline-3-spiro-4′-piperidine

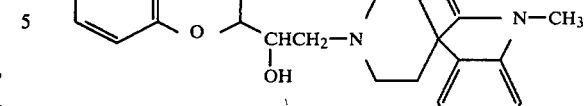

1′-[2-(6-methyl-1,4-benzodioxane-2-yl)-2-hydroxyethyl]-1-methyl-2-oxo-indoline-3-spiro-4′-piperidine

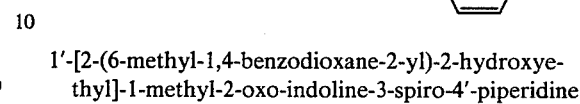

1′-[2-(6-methoxy-1,4-benzodioxane-2-yl)-2-hydroxyethyl]-1-methyl-2-oxo-indoline-3-spiro-4′-piperidine 1′-[2-(1,4-benzodioxane-2-yl)-2-hydroxyethyl]-2-oxo-1,2,5,6-tetrahydro-4H-pyrrolo[3,2,1-ij]quinoline-1-spiro-4′-piperidine

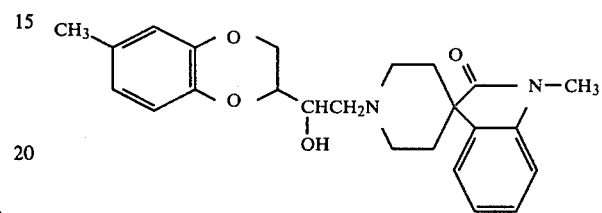

1′-[2-hydroxy-3-(1-naphthoxy)propyl]-2-oxo-1,2,5,6-tetrahydro-4H-pyrrolo[3,2,1-ij]quinoline-1-spiro-4′-piperidine 1′-[2-hydroxy-3-(1-naphthoxy)propyl]-1-ethyl-2-oxo-indoline-3-spiro-4′-piperidine 1′-[2-(1,4-benzodioxane-2-yl)-2-hydroxyethyl]-1-propyl-2-oxo-indoline-3-spiro-4′-piperidine 1′-[2-(1,4-benzodioxane-2-yl)-2-hydroxyethyl]-1-ethyl-2-oxo-indoline-3-spiro-4′-piperidine 1′-[2-(1,4-benzodioxane-2-yl)-2-hydroxyethyl]-1-methyl-indoline-3-spiro-4′-piperidine 1′-[2-hydroxy-3-(2-chlorophenoxy)propyl]-1-methyl-2-oxo-indoline-3-spiro-4′-piperidine 1′-[2-hydroxy-3-(2-methylphenoxy)propyl]-1-methyl-2-oxo-indoline-3-spiro-4′-piperidine 1′-[2-hydroxy-3-(2-methoxyphenoxy)propyl]-1-methyl-2-oxo-indoline-3-spiro-4′-piperidine 1′-[2-hydroxy-3-(2-cyano-phenoxy)propyl]-1-methyl-2-oxo-indoline-3-spiro-4′-piperidine 1′-[2-(1,4-benzodioxane-2-yl)-2-hydroxyethyl]-1-phenyl-2-oxo-indoline-3-spiro-4′-piperidine 1′-[2-hydroxy-3-(1-naphthoxy)propyl]-1-methyl-2-oxo-indoline-3-spiro-4′-piperidine 1′-[2-hydroxy-3-(1-naphthoxy)propyl]-1-ethylindoline-3-spiro-4′-piperidine 1′-(2-phenylethyl)-1-methylindoline-3-spiro-4′-piperidine

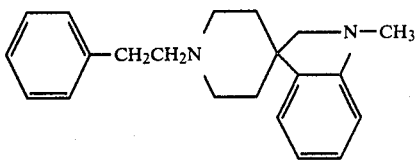

1'-[3-(4-fluorobenzoyl)propyl]-1-methyl-2-oxoindoline-3-spiro-4'-piperidine
1'-[3-(4-fluorobenzoyl)propyl]-1-ethyl-2-oxoindoline-3-spiro-4'-piperidine
1'-[3-(4-fluorobenzoyl)propyl]-1-propyl-2-oxoindoline-3-spiro-4'-piperidine
1'-[3-(4-fluorobenzoyl)propyl]-1-phenyl-2-oxoindoline-3-spiro-4'-piperidine
1'-[3-(4-fluorobenzoyl)propyl]-1-methyl-indoline-3-spiro-4'-piperidine
1'-[3-(4-fluorobenzoyl)propyl]-1-ethyl-indoline-3-spiro-4'-piperidine
1'-[4-(4-fluorophenyl)-4-hydroxybutyl)-1-methyl-2-oxoindoline-3-spiro-4'-piperidine
1'-[3-(3,4-dimethoxybenzoyl)propyl]-1-methyl-2-oxoindoline-3-spiro-4'-piperidine
1'-[3-(4-methoxybenzoyl)propyl]-1-methyl-2-oxoindoline-3-spiro-4'-piperidine
1'-[4-(3,4,5-trimethoxyphenyl)-4-hydroxybutyl]-1-methyl-2-oxo-indoline-3-spiro-4'-piperidine
1'-(2-phenoxyethyl)-1-ethyl-indoline-3-spiro-4'-piperidine
1'-[1-(4-benzyloxyphenyl)-1-hydroxypropane-2-yl]-1-methyl-2-oxo-indoline-3-spiro-4'-piperidine
1'-[1-(4-hydroxyphenyl)-1-hydroxypropane-2-yl]-1-methyl-2-oxo-indoline-3-spiro-4'-piperidine
1'-[2-(4-fluorobenzoyl)ethyl]-1-methyl-2-oxoindoline-3-spiro-4'-piperidine
1'-(1-phenylpropene-3-yl)-1-methyl-2-oxo-indoline-3-spiro-4'-piperidine
1'-(2-benzoylpropyl)-1-methyl-2-oxo-indoline-3-spiro-4'-piperidine
1'-[3-(4-fluorobenzoyl)propyl]-2-oxo-1,2,5,6-tetrahydro-4H-pyrrolo[3,2,1-ij]quinoline-1-spiro-4'-piperidine

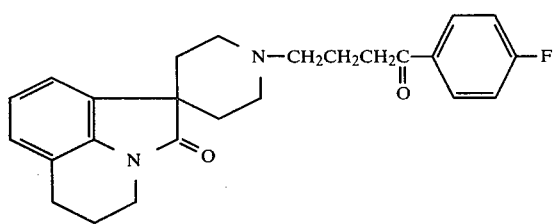

1'-[4-(4-fluorophenyl)-4-hydroxybutyl]-2-oxo-1,2,5,6-tetrahydro-4H-pyrrolo[3,2,1-ij]quinoline-1-spiro-4'-piperidine
1'-[3-(4-fluorobenzoyl)propyl]-1,2,5,6-tetrahydro-4H-pyrrolo[3,2,1-ij]quinoline-1-spiro-4'-piperidine
1'-benzoylmethyl-1,2,5,6-tetrahydro-4-pyrrolo[3,2,1-ij]quinoline-1-spiro-4'-piperidine
1'-(2-phenyl-2-hydroxyethyl)-1,2,5,6-tetrahydro-4H-pyrrolo[3,2,1-ij]quinoline-1-spiro-4'-piperidine
1'-(3-phenoxy-propyl)-1,2,5,6-tetrahydro-4H-pyrrolo[3,2,1-ij]quinoline-1-spiro-4'-piperidine
1'-(2-phenylethyl)-1,2,5,6-tetrahydro-4H-pyrrolo[3,2,1-ij]quinoline-1-spiro-4'-piperidine
1'-(3-(3,4-dimethylbenzoyl)propyl]-1-ethylindoline-3-spiro-4'-piperidine These spiro amine derivatives (I) in the free base form can be converted into their pharmaceutically acceptable salts such as acid addition salts of quaternary ammonium salts by treatment with mineral acids (e.g. hydrochloric acid, hydrobromic acid, phosphoric acid), organic acids (e.g. acetic acid, citric acid, oxalic acid, lactic acid, succinic acid, tartaric acid, cinnamic acid, ascorbic acid), alkyl halides, aralkyl halides or the like.

Each of the spiro amine derivatives (I) may be brought into a form suitable for administration according to a method known per se.

For the preparation of pharmaceutical compositions, they may be mixed with carriers or diluents such as water, sesame oil, calcium phosphate, starch, talcum, casein, magnesium stearate, methyl cellulose, polyglycols, tragacanth and the like, sometimes together with stabilizers and/or emulsifying agents.

The resulting mixture may be processed in usual manners to tablets, capsules, pills, ampoules and the like. The usual oral dosage is 1.0–500 mg per os daily.

Practical and preferred embodiments of the present invention are illustratively shown in the following examples, which are not intended to limit the scope of the invention thereto.

EXAMPLE 1

A mixture of 3.0 g of 4-chloro-1-(4-fluorophenyl)-1,1-ethylenedioxybutane, 2.0 g of 1-methyl-2-oxo-indoline-3-spiro-4'-piperidine, 2.8 g of anhydrous potassium carbonate, 0.1 g of potassium iodide and 30 ml of dimethylformamide was refluxed for 2 hours. The resulting mixture was poured into water and was extracted with ethyl acetate. The extract was washed with water, dried over anhydrous sodium sulfate and concentrated in vacuo. To the residual oil were added 60 ml of methanol, 20 ml of water and 10 ml of concentrated hydrochloric acid. The mixture was refluxed for 25 minutes and concentrated in vacuo. The residual oil was made alkaline with 28% aqueous ammonia and extracted with ethyl acetate. The extract was washed with water, dried over anhydrous sodium sulfate and concentrated. The residual oil was chromatographed over silica gel with ethyl acetate as an elueting agent to give 1'-[3-(4-fluorobenzoyl)propyl]-1-methyl-2-oxo-indoline-3-spiro-4'-piperidine, M.P. 95°–96.5° C.

EXAMPLE 2

In the same manner as in Example 1, the following compounds were obtained:
1'-[3-(4-methoxybenzoyl)propyl]-1-methyl-2-oxoindoline-3-spiro-4'-piperidine
M.P. 75°–79.5° C.
1'-[3-(3,4-dimethoxybenzoyl)propyl]-1-methyl-2-oxoindoline-3-spiro-4'-piperidine
M.P. 109°–112° C.
1'-[3-(4-fluorobenzoyl)propyl]-1-ethyl-2-oxoindoline-3-spiro-4'-piperidine
M.P. 104°–107° C.
1'-[3-(4-fluorobenzoyl)propyl]-1-propyl-2-oxoindoline-3-spiro-4'-piperidine
M.P. 90°–91° C.
1'-[3-(4-fluorobenzoyl)propyl]-1-methyl-indoline-3-spiro-4'-piperidine
M.P. 98°–103° C.
1'-[3-(4-fluorobenzoyl)propyl]-1-ethyl-indoline-3-spiro-4'-piperidine dihydrochloride M.P. 214°–216° C.
1'-[3-(4-fluorobenzoyl)propyl]-1-phenyl-2-oxoindoline-3-spiro-4'-piperidine
M.P. 116.5°–117° C.
1'-[3-(4-fluorobenzoyl)propyl]-2-oxo-1,2,5,6-tetrahydro-4H-pyrrolo[3,2,1-ij]quinoline-1-spiro-4'-piperidine
M.P. 105°–109° C.
1'-[3-(4-fluorobenzoyl)propyl]-1,2,5,6-tetrahydro-4H-pyrrolo[3,2,1-ij]quinoline-1-spiro-4'-piperidine dihydrochloride
M.P. 248°–249° C.

EXAMPLE 3

A mixture of 1.63 g of phenoxyethylchloride, 1.5 g of 1-methyl-2-oxo-indoline-3-spiro-4'-piperidine, 1.44 g of anhydrous potassium carbonate, 0.1 g of potassium iodide and 30 ml of dimethylformamide was stirred at 90°–100° C. for 5 hours. The resulting mixture was poured into water and was extracted with diethylether. The extract was washed with water, dried over anhydrous sodium sulfate and concentrated in vacuo. Thus obtained oil was treated with hydrochloric acid to give 1'-(2-phenoxyethyl)-1-methyl-2-oxo-indoline-3-spiro-4'-piperidine hydrochloride
M.P. 206°–210° C.

EXAMPLE 4

In the same manner as in Example 3, the following compounds were obtained:
1'-cinnamyl-1-methyl-2-oxo-indoline-3-spiro-4'-piperidine hydrochloride
M.P. 252°–255° C.
1'-(2-phenylethyl)-1-methyl-2-oxo-indoline-3-spiro-4'-piperidine hydrochloride
M.P. 167.5°–169° C.
1'-(2-phenylethyl)-1-methyl-indoline-3-spiro-4'-piperidine dihydrochloride
M.P. >280° C.
1'-(2-phenylethyl)-1-phenyl-2-oxo-indoline-3-spiro-4'-piperidine hydrochloride
M.P. 128°–137° C.
1'-[2-(4-fluorobenzoyl)ethyl]-1-methyl-2-oxoindoline-3-spiro-4'-piperidine hydrochloride
M.P. 196°–200° C.

EXAMPLE 5

A mixture of 0.4 g of 1'-[3-(4-fluorobenzoyl)propyl]-1-methyl-2-oxo-indoline-3-spiro-4'-piperidine, 1.0 g of sodium borohydride and 20 ml of isopropyl alcohol was refluxed for 30 minutes.

The resulting mixture was poured into water and was extracted with ethyl acetate. The extract was washed with water, dried over anhydrous sodium sulfate and concentrated in vacuo. The residual solid was washed with diisopropylether to give 1'-[4-(4-fluorophenyl)-4-hydroxybutyl]-1-methyl-2-oxo-indoline-3-spiro-4'-piperidine
M.P. 126.5°–127.5° C.

EXAMPLE 6

In the same manner as in Example 5, the following compounds were obtained:
1'-[4-(4-fluorophenyl)-4-hydroxybutyl]-2-oxo-1,2,5,6-tetrahydro-4H-pyrrolo[3,2,1-ij]quinoline-1-spiro-4'-piperidine
M.P. 137°–141° C.
1'-[4-(3,4-dimethoxyphenyl)-4-hydroxybutyl]-1-methyl-2-oxo-indoline-3-spiro-4'-piperidine
M.P. 114°–122° C.
1'-[4-(4-fluorophenyl)-4-hydroxybutyl]-1-ethyl-2-oxoindoline-3-spiro-4'-piperidine
M.P. 131°–134° C.

EXAMPLE 7

A mixture of 3.8 g of p-benzyloxy-α-bromopropiophenone, 2 g of 1-methyl-2-oxo-indoline-3-spiro-4'-piperidine, 2 g of sodium bicarbonate and 30 ml of dimethylformamide was stirred for 5 hours at room temperature.

The resulting mixture was poured into water and was extracted with ethylacetate. The extract was washed with water, dried over anhydrous sodium sulfate and concentrated in vacuo. Thus obtained oil was washed with n-hexane to give 1'-[1-(4-benzyloxybenzoyl)ethyl]-1-methyl-2-oxo-indoline-3-spiro-4'-piperidine
IR $\nu_{C=O}$ 1680–1710 cm$^{-1}$

EXAMPLE 8

A mixture of 4.5 g of 1'-[1-(4-benzyloxybenzoyl)ethyl]-1-methyl-2-oxo-indoline-3-spiro-4'-piperidine, 5.6 g of sodium borohydride and 150 ml of isopropylalcohol was refluxed for 1 hour. The resulting mixture was poured into water and was extracted with ethylacetate. The extract was washed with water, dried over anhydrous sodium sulfate and concentrated in vacuo. The crude solid was recrystallized from ethanol to give 1'-[1-(4-benzyloxyphenyl)-1-hydroxypropane-2-yl]-1-methyl-2-oxo-indoline-3-spiro-4'-piperidine.
M.P. 195°–199° C.

And the mother liquor was concentrated in vacuo and was chromatographed over silica gel to give the isomer.
M.P. 93.5°–98.5° C.

EXAMPLE 9

A mixture of 0.7 g of 1'-[1-(4-benzyloxyphenyl)-1-hydroxypropane-2-yl]-1-methyl-2-oxo-indoline-3-spiro-4'-piperidine (melting point 195°–199° C.), 0.1 g of 10% palladium on charcoal and 120 ml of ethanol was vigorously stirred under atmospheric hydrogen at room temperature, until an equimolar amount of hydrogen was consumed. The catalyst was filtered off, and the filtrate was concentrated in vacuo.

Thus obtained solid was washed with diisopropyl ether to give 1'-[1-(4-hydroxyphenyl)-1-hydroxypropane-2-yl]-1-methyl-2-oxo-indoline-3-spiro-4'-piperidine
M.P. 223°–225° C.

EXAMPLE 10

A mixture of 1.7 g of 1-phenoxy-2,3-epoxypropane, 2 g of 1-methyl-2-oxo-indoline-3-spiro-4'-piperidine and 120 ml of ethanol was refluxed for 3 hours. The resulting mixture was concentrated and crystallized from diisopropylether to give 1'-(2-hydroxy-3-phenoxypropyl)-1-methyl-2-oxo-indoline-3-spiro-4'-piperidine
M.P. 104°–110° C.

EXAMPLE 11

In the same manner as in Example 10, the following compounds were obtained:
1'-[2-hydroxy-3-(1-naphthoxy)propyl]-1-methyl-2-oxo-indoline-3-spiro-4'-piperidine
M.P. 148.5°–150.5° C.

1'-[2-hydroxy-3-(1-naphthoxy)propyl]-2-oxo-1,2,5,6-tetrahydro-4H-pyrrolo[3,2,1-ij]quinoline-1-spiro-4'-piperidine
M.P. 113°–119° C.

1'-[2-hydroxy-3-(1-naphthoxy)-propyl]-1-ethylindoline-3-spiro-4'-piperidine
M.P. 114°–118° C.

EXAMPLE 12

A mixture of 2.9 g of 1-(1,4-benzodioxane-2-yl)2-bromoethanol, 2 g of 1-methyl-2-oxo-indoline-3-spiro-4'-piperidine, 1.9 g of sodium carbonate and 30 ml of dimethylformamide was stirred for 1.5 hours at 100° C. The resulting mixture was poured into water and extracted with ethyl acetate. The extract was washed with water, dried over anhydrous sodium sulfate and concentrated in vacuo.

The residual oil was chromatographed over silica gel and washed with diisopropylether to give 1'-[2-(1,4-benzodioxane-2-yl)-2-hydroxyethyl]-1-methyl-2-oxo-indoline-3-spiro-4'-piperidine
M.P. 113°–128° C.

EXAMPLE 13

In the same manner as in Example 12, 1'-[2-(1,4-benzodioxane-2-yl)-2-hydroxyethyl]-2-oxo-1,2,5,6-tetrahydro-4H-pyrrolo[3,2,1-ij]quinoline-1-spiro-4'-piperidine was obtained.
M.P. 197°–207° C.

REFERENTIAL EXAMPLE (A) 13 g of sodium amide was added to a mixture of 20 g of N-methyloxindole, 32 g of N,N-di-(2-chloroethyl)benzylamine and 130 ml of toluene at room temperature while stirring, and the mixture was heated under reflux for 3 hours.

After the reaction was completed, diluted aqueous hydrochloric acid solution was added dropwise to the reaction mixture slowly to decompose the unreacted, excessive sodium amide under cooling with ice. The precipitated solid was collected, washed with water and benzene, and was converted to the corresponding free base by shaking with aqueous ammonia solution and ethylacetate. The ethylacetate layer was washed with water, dried over anhydrous sodium sulfate and concentrated in vacuo. Thus obtained oil was chromatographed over silica gel to give 1'-benzyl-1-methyl-2-oxo-indoline-3-spiro-4'-piperidine
I.R. $\nu cm^{-1}$ 1700 cm$^{-1}$ (B) In the same manner as (A), the following compounds were obtained:
1'-benzyl-1-ethyl-2-oxo-indoline-3-spiro-4'-piperidine
IR $\nu cm^{-1}$ 1700–1710 cm$^{-1}$
1'-benzyl-1-propyl-2-oxo-indoline-3-spiro-4'-piperidine
IR $\nu cm^{-1}$ 1705 cm$^{-1}$
1'-benzyl-1-phenyl-2-oxo-indoline-3-spiro-4'-piperidine
IR $\nu cm^{-1}$ 1705 cm$^{-1}$
1'-benzyl-2-oxo-1,2,5,6-tetrahydro-4H-pyrrolo[3,2,1-ij]quinoline-1-spiro-4'-piperidine
IR $\nu cm^{-1}$ 1700 cm$^{-1}$ (C) A mixture of 15.1 g of 1'-benzyl-1-methyl-2-oxoindoline-3-spiro-4'-piperidine, 33.5 g of benzyloxycarbonyl chloride and 530 ml of toluene was refluxed for 6 hours. The resulting mixture was poured into water and extracted with ethylacetate. The extract was washed with water, dried over anhydrous sodium sulfate and concentrated in vacuo. Thus obtained oil was washed with n-hexane to give 1'-benzyloxycarbonyl-1-methyl-2-oxo-indoline-3-spiro-4'-piperidine.

A mixture of 12 g of the above obtained solid, 21.6 g of water, 7.2 g of 5% palladium on charcoal and 500 ml of ethanol was vigorously stirred under atmospheric hydrogen at room temperature, until the reaction was completed. The catalyst was filtered off, and the filtrate was concentrated in vacuo. Thus obtained solid was washed with diisopropylether to give 1-methyl-2-oxo-indoline-3-spiro-4'-piperidine.
M.P. 146°–151° C.

What is claimed is:

1. A compound of the formula

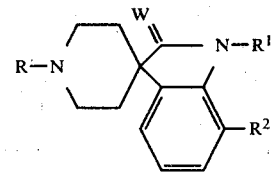

wherein $R^1$ is a hydrogen atom, a $C_1$–$C_4$ alkyl group, a phenyl group, or a phenyl group substituted with a halogen atom, a $C_1$–$C_4$ alkyl group or a $C_1$–$C_4$ alkoxy group, $R^2$ is a hydrogen atom, or $R^1$ and $R^2$, when taken together, may form a $C_1$–$C_4$ alkylene group, W is an oxygen atom or two hydrogen atoms and R is selected from the group consisting of the formula:

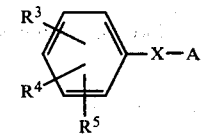

wherein A is a $C_1$–$C_4$ alkylene group, X is a carbonyl group, an oxygen atom, a single bond linkage, the formula >CH—OH or the formula —CH=CH— and $R^3$, $R^4$ and $R^5$ are each independently hydrogen, methyl, ethyl, isopropyl, butyl, methoxy, ethoxy, isopropoxy, halogen, hydroxy or benzyloxy, provided that when any one of $R^3$, $R^4$ and $R^5$ is benzyloxy, the other two are hydrogen, and the formula:

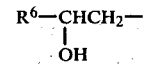

wherein $R^6$ is a group of the formula:

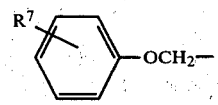

wherein $R^7$ is a hydrogen atom, a halogen atom, a nitrile group, a $C_1$–$C_4$ alkyl group, a $C_1$–$C_4$ alkoxy group or a hydroxy group,

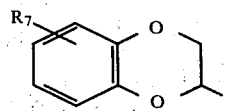

wherein $R^7$ is as defined above, or

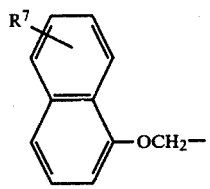

wherein R⁷ is as defined above, and the non-toxic pharmaceutically acceptable acid addition salts thereof.

2. The compound according to claim 1, wherein W is an oxygen atom.

3. The compound according to claim 1, wherein R is a group of either one of the formulae:

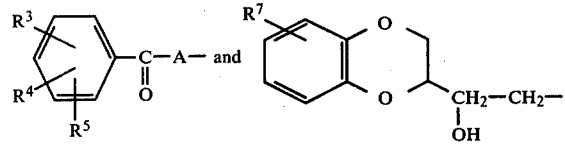

(wherein $R^3$, $R^4$, $R^5$, A and $R^7$ are each as defined in claim 1).

4. The compound according to claim 1, wherein W is an oxygen atom and R is the formula:

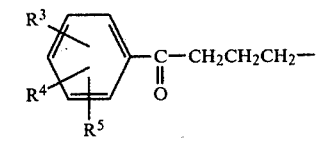

(wherein $R^3$, $R^4$ and $R^5$ are each as defined in claim 1).

5. The compound according to claim 1, wherein W is an oxygen atom and R is the formula:

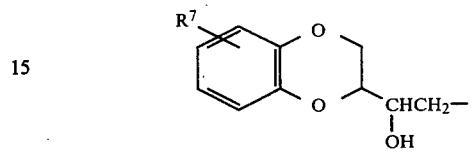

(wherein $R^7$ is as defined in claim 1).

6. 1'-[3-(4-fluorobenzoyl)propyl]-1-methyl-2-oxoindoline-3-spiro-4'-piperidine.

7. 1'-[3-(4-fluorobenzoyl)propyl]-1-propyl-2-oxoindoline-3-spiro-4'-piperidine.

8. 1'-(2-hydroxy-3-phenoxypropyl)-1-methyl-2-oxoindoline-3-spiro-4'-piperidine.

9. 1'-[3-(4-fluorobenzoyl)propyl]-2-oxo-1,2,5,6-tetrahydro-4H-pyrrolo[3,2,1-ij]quinoline-1-spiro-4'-piperidine.

10. 1'-[2-(1,4-benzodioxane-2-yl)-2-hydroxyethyl]-1-methyl-2-oxo-indoline-3-spiro-4'-piperidine.

11. 1'-[2-(1,4-benzodioxane-2-yl)-2-hydroxyethyl]-2-oxo-1,2,5,6-tetrahydro-4H-pyrrolo[3,2,1-ij]quinoline-1-spiro-4'-piperidine.

12. A pharmaceutical composition comprising at least one compound as claimed in claim 1 and their pharmaceutically acceptable salts, in an amount which is antihypertensively effective or effective as a central nervous system depressant and at least one pharmaceutically acceptable diluent or carrier.

* * * * *